(12) United States Patent
Hoctor et al.

(10) Patent No.: US 9,538,987 B2
(45) Date of Patent: Jan. 10, 2017

(54) SYSTEM AND METHOD FOR ULTRASOUND IMAGING

(75) Inventors: Ralph Thomas Hoctor, Saratoga Springs, NY (US); Larry Yiu Lau Mo, Latham, NY (US)

(73) Assignee: General Electric Company, Schenectady, NY (US)

( * ) Notice: Subject to any disclaimer, the term of this patent is extended or adjusted under 35 U.S.C. 154(b) by 1106 days.

(21) Appl. No.: 13/247,183

(22) Filed: Sep. 28, 2011

(65) Prior Publication Data

US 2013/0079639 A1 Mar. 28, 2013

(51) Int. Cl.
| | |
|---|---|
| *G06F 17/00* | (2006.01) |
| *A61B 8/08* | (2006.01) |
| *A61B 8/00* | (2006.01) |
| *G01S 7/52* | (2006.01) |
| *G01S 15/89* | (2006.01) |

(52) U.S. Cl.
CPC ........... *A61B 8/5207* (2013.01); *A61B 8/4477* (2013.01); *G01S 7/52025* (2013.01); *G01S 7/52047* (2013.01); *G01S 15/8915* (2013.01)

(58) Field of Classification Search
CPC .............. G01S 15/8915; G01S 15/8997; G01S 7/52047; A61B 2019/5276; A61B 8/4461; G10K 11/346
USPC .................................. 341/140–170; 600/447
See application file for complete search history.

(56) References Cited

U.S. PATENT DOCUMENTS

| | | | |
|---|---|---|---|
| 4,839,652 A * | 6/1989 | O'Donnell et al. | .......... 341/122 |
| 5,179,455 A | 1/1993 | Garlick | |
| 5,477,859 A | 12/1995 | Engeler | |
| 5,951,479 A | 9/1999 | Holm et al. | |
| 6,551,246 B1 | 4/2003 | Ustuner et al. | |
| 6,860,855 B2 | 3/2005 | Shelby et al. | |
| 8,002,705 B1 | 8/2011 | Napolitano et al. | |

OTHER PUBLICATIONS

Jensen et al., "Spatial Filters for Focusing Ultrasound Images", IEEE International Ultrasonics Symposium, vol. 2, pp. 1507-1511, Oct. 7-10, 2001.

(Continued)

*Primary Examiner* — Elmer Chao
(74) *Attorney, Agent, or Firm* — Dean D. Small; The Small Patent Law Group, LLC (57) ABSTRACT

Embodiments presented herein describe a method, a system and a computer program product for ultrasound imaging. The method in one example includes receiving a plurality of ultrasound echo signals from a plurality of transducer elements in response to ultrasound transmit beams. The method computes beam sums of ultrasound echo signals originating from a point to be imaged, for the corresponding ultrasound transmit beams. The method generates a time record comprising a plurality of beam sums, wherein the time record includes beam sums corresponding to multiple instants of time in a time window. The method filters the time record based, at least in part, on a predetermined response function. Finally, the method reconstructs the point to be imaged based on one or more of the filtered time records corresponding to one or more of the plurality of ultrasound transmit beams. The method repeats this process for each point to be imaged.

7 Claims, 5 Drawing Sheets

(56) References Cited

OTHER PUBLICATIONS

Kim et al., "Beamforming using Spatial Matched Filtering with Annular Arrays (L)", Journal of the Acoustical Society of America, vol. 121, Issue 4, pp. 1852-1855, Apr. 2007.

Kim et al., "Efficient Array Beam Forming by Spatial Filtering for Ultrasound B-Mode Imaging", Journal of the Acoustical Society of America, vol. 120, Issue 2, pp. 852-861, Aug. 2006.

Liu et al., "SNR Comparisons of Beamforming Strategies", IEEE transactions on Ultrasonics, Ferroelectrics and Frequency Control, vol. 54, Issue 5, pp. 1010-1017, May 2007.

Zemp et al., "Imaging with Unfocused Regions of Focused Ultrasound Beams", Journal of the Acoustical Society of America, vol. 121, Issue 3, pp. 1491-1498, Mar. 2007.

Moo-Ho Bae et al.; "A New Ultrasonic Synthetic Aperture Tissue Harmonic Imaging System"; 2008 IEEE International Ultrasonics Symposium Proceedings; 4 Pages.

Moo-Ho Bae et al.; "A Study of Synthetic-Aperture Imaging with Virtual Source Elements in B-Mode Ultrasound Imaging Systems"; IEEE Transactions on Ultrasonics, Ferroelectrics, and Frequency Control, vol. 47, No. 6, Nov. 2000; pp. 1510-1519.

Gabriel Montaldo et al.; "Coherent Plane-Wave Compounding for Very High Frame Rate Ultrasonography and Transient Elastography"; IEEE Transactions on Ultrasonics, Ferroelectrics, and Frequency Control, vol. 56, No. 3, Mar. 2009; pp. 489-506.

Sverre Holm et al.; "Improved framerate with synthetic transmit aperture imaging using prefocused subapertures"; to Appear in Proc. IEEE Ultrason. Symp., Toronto, Oct. 1997; 4 Pages.

Ralph Hoctor; "High Frame-Rate Synthetic Transmit Focus of Ultrasound Array Imaging using a RAKE Receiver"; GE Document; 25 Pages.

Chuck Bradley; "Retrospective Transmit Beamformation"; Aug. 2008; 8 Pages.

Catherine H. Frazier; "Synthetic Aperture Techniques with a Virtual Source Element"; IEEE Transactions on Ultrasonics, Ferroelectrics, and Frequency Control, vol. 45, No. 1, Jan. 1998; pp. 196-207.

* cited by examiner

SYSTEM AND METHOD FOR ULTRASOUND IMAGING

BACKGROUND

Embodiments presented herein relate generally to ultrasound imaging systems, and more particularly to synthetic transmit focusing of ultrasound images.

Ultrasound imaging is widely used for non-invasive imaging of interior portions of the human body. Medical ultrasound imaging, also known as ultrasonography, is a diagnostic medical imaging technique for visualizing the cardiovascular system and other internal organs and structures with real time images, both two-dimensional (planar) and three-dimensional (volumetric). When used to image the cardiovascular system, heart mechanics, valve motion and blood flow can be visualized in real time. When used to visualize major organs, their size, structure and any pathological lesions can be observed. Ultrasound is also used to form volumetric images of fetuses during routine and emergency prenatal care.

Ultrasound imaging systems may use a transmit array to transmit ultrasound pulses, a receive array to receive echoes of the transmitted ultrasound pulses, and an image reconstruction system to translate the received echoes into images. In most systems, the transmit and receive arrays are the same physical device, and a means exists for switching the device between a transmit mode of operation and a receive mode of operation. An image is typically formed by scanning a beam. That is, beams of ultrasound pulses are formed in a sequence of beamsteering angles with respect to the array normal and a focused transmission and reception occurs in each such direction. The resulting sequence of one-dimensional data sets represents reflectivity data as a function of range in each of the beam directions. This measured acoustic echo data set covers a two-dimensional patch of the reflectivity distribution in front of the array and can be converted into a displayable image.

The standard approach to image reconstruction using such a data set typically involves scan conversion, a process by which samples of demodulated, formed beams are interpolated from a range/angle grid into a rectilinear one. An alternative scheme is the direct reconstruction of image samples in an arbitrary output arrangement that could be rectilinear. Such direct reconstruction may be better for software image formation on massively parallel processors, while the standard method may be better suited to special purpose hardware. The basic operation of forming a single sample is the same for both approaches, although it may typically be implemented differently.

The image feature corresponding to a point reflector is called the point spread function (PSF) of the system. The size of the PSF is often used as an indicator of the potential image quality of a system. The dimensions of the PSF of an ultrasound system are different in two orthogonal directions: the axial response along the direction of sound propagation is determined by the duration of the ultrasound pulse, and the lateral response transverse to the propagation direction is determined by the transmit and receive focal properties at the depth of the point of interest. At any point in the image, the PSF is the product of a transmit point response with a receive point response. The receive lateral point response can be dynamically adjusted, during reception of the acoustic data or at the time of image reconstruction so that every point in the image is in good receive focus. Such a dynamic adjustment is standard practice in modern ultrasound imaging equipment. In a scan-converter-based system, dynamic receive focus is typically done during the reception of the acoustic data. In a direct reconstruction system, array element data may be recorded which allows dynamic receive focus to be performed for every reconstructed output sample. In either case, reconstructed samples are all individually receive focused. The transmit lateral point response depends on the aperture size and the delay structure used to form the transmit beam.

Most ultrasound imaging systems focus the transmit array to a fixed depth of interest, in order to maximize lateral resolution at that depth. The echoes received from a depth corresponding to the transmit focus can form relatively sharp images, while those received from other depths will produce more lateral spread in the PSF. Just as in an optical lens system, the more highly focused a transmit beam is, the smaller the depth of field over which the tightest focus is observed. Thus, the resolution of the image based on focused ultrasound transmit beams is not uniform and degrades as a function of the difference between the depth of the point of interest and the focal depth.

Some known systems reconstruct an image using multiple transmit focal zones to form an image with uniformly high resolution at all depths. Such a procedure requires the transmission of multiple ultrasound beams for each beamsteering direction, which causes delays in the generation of a complete image and consequentially reduces the frame rate.

For some years, there has been interest in the concept of reconstructing focused images without using the multiple focal zone approach. Such a technique would allow the formation of a highly focused image at higher frame rates than are currently available. In general, such techniques are known as synthetic transmit focus imaging. Typically, the image reconstruction system may coherently superpose the receive data obtained from multiple transmit beams, each beam corresponding to different beamsteering and/or transmit focus characteristics, to synthesize images that are in focus at all ranges. Schemes of this kind can be implemented in both standard image formation systems and direct reconstruction systems.

The most basic synthetic focusing technique is called by a variety of names, including "N-squared synthesis", "direct synthesis" or just "synthetic focusing", and consists of transmitting from each of a set of transmit elements and receiving the echoes from each transmission at a set of receive elements. In a typical monostatic (reflection mode) case, both sets of elements correspond to the elements of a single transmit/receive array. The N-squared approach has been called the "gold standard" because every reconstructed point is in full transmit/receive focus and, in principle, no image formed with the same array can have a better focus. More recently, this approach has been called the "total focus method" ("TFM").

The earliest synthetic focus acoustical imaging procedure was called the synthetic aperture focusing technique (SAFT). SAFT consists of scanning a single transmit/receive element over the aperture plane and recording the received waveform at every transmit position. If the transmit/receive aperture is an array, this corresponds to transmitting with each element and recording the echoed data only at the transmit element, thus, SAFT measurements are a subset of TFM measurements.

In general, SAFT and TFM both require many transmits to form an image, and this can present problems when the reflectivity distribution is in motion, since the measurements have to be coherently combined. Additionally, single element transmits typically result in poor penetration. A compromise method that uses fewer, higher-intensity transmits is that of coherent compounding of transmit wavefronts from focused and unfocused beams. In these schemes a multi-element subarray is used to insonify the reflectivity distribution, and the data from multiple transmits, possibly in different beamsteering directions, is coherently compounded by, for example, adding complex analytic signal values derived from multiple dynamic receive beamformers focused at a single point in space. In general, these schemes are approximations to TFM.

All of these known synthetic focus techniques make use of data sets that are unique to them, rather than using the scanned beam data set employed in standard ultrasound imaging. In the recent past, there has been interest in the concept of reconstructing focused images using unfocused portions of transmitted ultrasound beams in the standard, scanned-beam data set. This approach is called retrospective transmit focus (RTF) as opposed to synthetic transmit focus. Naturally, RTF is attractive to manufacturers with an existing base of ultrasound imaging equipment, since the transmit beamforming subsystem of an existing instrument does not have to be modified in order to migrate that instrument to RTF operation.

One such scheme uses the converging portions of focused beams to perform a synthesis. Another coherent compounding approach is based on planewave insonification. In general, since such prior art techniques are based on spatial compounding of unfocused beams, the resulting synthetic PSF can have reduced contrast due to high sidelobes, which are in turn due to the lack of transmit focus of the component transmit beams. This is because portions of propagating wavefronts not used for mainlobe synthesis contribute very energetic transmit sidelobes that can extend far from the synthesized PSF mainlobe, in some cases.

Some known techniques use a spatial or spatial/temporal matched filter on every element of the receive array, prior to receive beamforming to reduce the effective transmit response away from the point to be reconstructed. The associated synthetic transmit focus schemes have used SAFT, so these are not RTF approaches. The filter is matched to the expected reflection from a point to be imaged. Such a technique is known to result in a slight loss of axial resolution.

The propagation of ultrasound in fluids can be highly nonlinear, and this nonlinearity results in high-amplitude propagating ultrasound waves being converted from purely harmonic waves to sawtooth waves. This change of shape results in a transfer of energy from the fundamental frequency region of the energy spectrum to the regions near the harmonic frequencies. A standard mode of operation in modern imaging instruments is to select the second (or higher) harmonic portion of the received signal by filtering or other means and use the selected portion of the reflection signal for imaging. This mode of operation is called tissue harmonic imaging (THI). It would be advantageous for any RTF scheme to operate in THI mode as well as in fundamental imaging mode.

Therefore, there is a need for an ultrasound imaging system that produces highly focused images with the high contrast. There is also a need for a system that operates from low PSF sidelobes at all depths, at high frame rates, using standard arrays and transmission schemes, and operating in both fundamental and THI modes.

BRIEF DESCRIPTION

Embodiments presented herein describe a method and a system for ultrasound imaging. The method includes receiving a plurality of ultrasound echo signals in response to a set of fixed-focus ultrasound transmit beams in a plurality of beamsteering directions. Such transmissions may be focused at infinity or at a depth in the nearfield of the aperture. Each of the plurality of ultrasound echo signals is received at a corresponding ultrasound transducer array element. The method further includes computing a fixed-focused, coherent beam sum for reception of the echo originating from a single location in the reflectivity distribution, based on the plurality of ultrasound echo signals, wherein the beam sum comprises the time-skewed, phase-sensitive summation of a plurality of ultrasound echo signals received from a predefined ultrasound transmit beam. For each reconstructed sample, the coherent beam sum is performed for multiple increments of time without changing the spatial focus, producing a time record, the duration of which is determined by the duration of the expected insonification at the point in space on which the receive beamformer is focused.

For each of one or more such time records corresponding to different transmit beams and receive-focused on the same point of interest, the method reconstructs an integration window consisting of a vector of samples of RF data by forming the inner product of the time record with a numerical representation of the expected received echoed insonification at the point to be imaged or some other predetermined response function associated with the point to be imaged. This inner product operation is performed for each point in the integration window. Next, the reflectivity at the point to be imaged is reconstructed by pointwise addition all of the output integration windows, each corresponding to a single transmit beam. Next, the method reconstructs a sample of the output ultrasound image by envelope demodulation of the RF signal in the integration window. Finally, the method reconstructs an ultrasound image or pre-image data set by generating all of the reconstructed spatial samples associated with a single frame having an arbitrary given spatial sampling pattern.

In some embodiments, the predefined response function serving as the inner product kernel operating on the output time record produced by the receive beamformer is decomposed into the convolution of the waveform transmitted and received by a single array element and a second vector representing the time dispersion of the insonifying waveform due to the position of the point to be imaged on the unfocused ultrasound beam. The inner product operation can then be implemented as a convolution of the receive-beamformed ultrasound data with the first vector representing the waveform transmitted and received by a single array element, followed by an inner product operation between the second vector and a selected section of the filtered, beam-summed ultrasound data, the section selected to correspond to the time dispersion due to lack of transmit focus expected at a particular point in space that is of interest.

In some other embodiments, the matched filter operation whose impulse response represents the single transmitted and received pulse is implemented on the signal from each receive array element, prior to formation of the coherent beam sum.

In some other embodiments, the matched filter operation implemented on the signal from each receive array element, prior to formation of the coherent beam sum, has an impulse response representing the second or higher harmonic component of an incident ultrasound waveform distorted by nonlinear propagation from the array to the point of reflection.

In some embodiments, the signal measured at the individual receive array element is sampled at an RF sample rate, while in other embodiments, the signal is converted to a low-pass in-phase and quadrature representation and re-sampled at a lower rate. In embodiments in which the signal is converted to an in-phase and quadrature representation, the receive beamformer performs analytic signal reconstruction and the output of the subsequent matched filter operation is a single sample of a beamformed analytic signal. In such systems the step of demodulating the sum of output samples is performed by computing the modulus of the complex signal and the integration window has unity length. In some embodiments using in-phase and quadrature representation, the matched filter for a single transmitted and received pulse is incorporated into the circuit for conversion of the RF signal into the in-phase and quadrature representation.

In some other embodiments, the single-pulse matched filter whose impulse response represents the transmitted and received pulse from a single array element is replaced by a filter whose frequency response is that of a bandpass filter whose passband is centered on the transmitted RF center frequency and whose bandwidth is greater than or equal to the effective bandwidth of the transmitted ultrasound. In such embodiments, this approximate matched filter is applied to the signal from each receive array element, prior to formation of the coherent beam sum.

In some other embodiments, the single-pulse matched filter whose impulse response represents the transmitted and received pulse from a single array element is replaced by a filter whose frequency response is that of a bandpass filter whose passband is centered on the second or higher harmonic frequency of the transmitted ultrasound and whose bandwidth is greater than or equal to the effective bandwidth of the transmitted ultrasound. In such embodiments, this approximate matched filter is applied to the signal from each receive array element, prior to formation of the coherent beam sum.

In some other embodiments, the single-pulse matched filter whose impulse response represents the transmitted and received pulse from a single array element is replaced by a filter whose impulse response is the transmit excitation applied to each individual transmit array element. In such embodiments, this approximate matched filter is applied the signal from each receive array element, prior to formation of the coherent beam sum.

In some other embodiments, the single-pulse matched filter whose impulse response represents the transmitted and received pulse from a single array element is omitted. In such embodiments, the second filter representing the time dispersion due to lack of transmit focus expected at a particular point in space that is of interest is applied at the output of the receive beamformer just as in embodiments that have a single-pulse matched filter or approximate matched filter.

In some other embodiments, the single-pulse matched filters are matched to the second or higher harmonic components of a reflected insonifying waveform that has been distorted by propagation through a nonlinear medium. In some of these embodiments, the single-pulse matched filter impulse response is the harmonic component of the single-element transmitted pulse as modified by nonlinear propagation followed by reception at an array element, in a frequency band corresponding to the harmonic component desired for image formation. In other such embodiments, the composite matched filter applied at the output of the receive beamformer is the second or higher harmonic component of the incident ultrasound waveform at the point of interest as received at a single array element. In other such embodiments, the receive element data is bandpass filtered to extract the second or higher harmonic component, and the single-pulse matched filter is omitted. In yet other embodiments, double transmissions with pulse inversion are used and the harmonic components are extracted by summation of the received data, and in such embodiments the single-pulse matched filter is omitted.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Medical ultrasound imaging systems are widely used for performing diagnostic procedures. Typically, the utility of such systems is enhanced by sharper images and images that have higher contrast. Additionally, the depiction of tissue motion is enhanced when the rate at which individual frames of the image sequence are displayed, know as the frame rate, is increased. As presented herein a technical effect of the described systems and methods of ultrasound imaging is to produce more highly focused images at higher frame rates than conventional ultrasound imaging systems while reducing imaging sidelobes, which consequently increases image contrast. Ultrasound imaging systems may employ phased array imaging or translated aperture imaging. Embodiments presented herein apply to both, the phased array imaging technique and the translated aperture imaging technique.

While exemplary descriptions include RAKE filtering, embodiments presented herein form highly focused images using retrospective transmit focusing (RTF) combined with compression of the received, reflected waveforms in the time domain. In other words, various embodiments presented herein form transmit/receive focused image samples using reflected energy from the unfocused portions of transmit-focused beams.

An ultrasound beam formed by transmission from a transducer array is said to be focused at those regions of space for which all the wavelets transmitted by the individual array elements add up in phase. At the focal point, the wavelets from all the transducer array elements add in phase, while at points with distances less than the focal distance and angles near the beamsteering angle, transmissions from only at most a subset of adjacent transducer array elements add in phase. Thus a coherent wavefront that converges as it propagates to the focal point is formed. At depths greater than the focal distance, the wavefront diverges. Taken together, these wavefronts constitute the ultrasound beam.

Coherent compounding techniques that use focused transmissions sum together reflections generated by these converging and diverging wavefronts. Because the region that is illuminated by each such wavefront is larger than the point to be imaged, the effect of coherent compounding by itself is to synthesize an imaging point spread function that may have high sidelobes relative to the point spread function at the transmit focus. The high sidelobe level in the synthesized PSF can be lowered by combining a large number of transmits, but in the standard RTF data acquisition set-up, this implies a large number of transmits, which will reduce the framerate if an image is to be formed at a substantial depth.

At an arbitrary point in space, the insonifying waveform is the superposition of the transmitted wavelets from all the array elements, delayed by their respective propagation times and modified by any propagation effects. This is also approximately true for nonlinear propagation environments where superposition does not hold, except that in that case low amplitude portions of the insonifying waveform are distorted less than high amplitude portions, and so contribute less energy to the harmonic frequency bands. When a waveform incident at a certain point in space is dispersed in time, the maximum amplitude of the insonification is low and the transmit beam is considered to be unfocused at that point.

The waveform incident at a point in space where the transmit beam is unfocused is analogous to the signaling waveform used by a digital communications system that has passed through a multipath channel. Such a channel causes the reception of the coherent sum of multiple copies of a signaling waveform transmitted through the channel to arrive at the receiver. This analogy between insonification of a point in space at which the transmit beam is unfocused and reception of a waveform that has passed through a multipath channel allows the application of communications systems techniques involving the use of matched filters to ultrasound imaging. A matched filter is a filter, the impulse response of which is matched to a certain waveform of interest. Matched filters are applied in signal detection because their use maximizes the output signal-to-noise ratio when applied to a waveform observed in additive noise.

The use of matched filters for reception of known waveforms is common practice in the field of Digital Communications. A digital communications system typically transmits one of an ensemble of known signaling waveforms to signify a symbol associated with one or more bits of information. At the receiver, the signaling waveform is demodulated by projection onto a set of basis vectors representing the ensemble of signaling waveforms. The projection operator used for this demodulation is a matched filter with a finite impulse response. Since the output of a matched filter is a convolution of the input and the impulse response, the interpretation of the matched filter as a projection operator is only valid when the output is sampled at a time instant for which the matched filter response to the waveform for which it is matched has reached its maximum, and the receiver typically has to estimate the correct phase of a sample clock to measure samples at these instants. The approximation of such matched filters in various ways, for example by simple bandpass filters, is well-known in the fields of radio and radar.

When a digital transmission takes place through a multipath channel, multiple versions of the transmitted waveform arrive at the receiver coherently summed with each other, and each component incurs a different delay. If the channel characteristics are known, the receiver can, in principle, construct a matched filter or other predefined response function for the signaling waveform at the output of the channel. In the case of the ultrasound imaging system of one embodiment, such a predefined response function is constructed for every location in space and for every transmit beam that the system will combine to form an image of that point. The delay characteristics of the physical multipath propagation to that point are approximated using a nominal speed of sound and the imaging geometry for every point to be imaged and every transmit beam that is to be used to reconstruct that point. The resulting matched filter based on the predefined response function is applied to the measured data at the time corresponding to the echo of the first-arriving wavelet. The ensemble of filter impulse responses obtained in this way is stored in memory and each is used when the associated sample is to be reconstructed.

However, an advantageous alternative implementation involves a signal processing structure that is known as a RAKE receiver, which takes advantage of the fact that the input waveform is a multiple superposition of a simpler component waveform. If such a superposition is matched-filtered for the component waveform, the output is a superposition of delayed instances of the pulse autocovariance function, which has a peak value proportional to the energy in the component waveform. If the output waveform from the component waveform matched filter is sampled at the instants corresponding to these peaks and the samples are added, the effect of the original matched filter sampled at the peak output is produced. Such a sampling scheme can be implemented as a Finite Impulse Response (FIR) filter, sometimes referred to as a RAKE FIR filter. In general, a broadband component waveform allows paths with short delay difference to be resolvable, and for this reason RAKE receivers are often paired with direct sequence spread spectrum transmissions. The wavelets emitted by elements of an ultrasound array are typically broadband waveforms of short duration. The RAKE filter is sampled uniformly at an interval corresponding to the temporal resolution limit (the inverse of the signaling bandwidth) and it interpolates the timing phase of the single-pulse matched filter for each transmission path.

Figure 1:
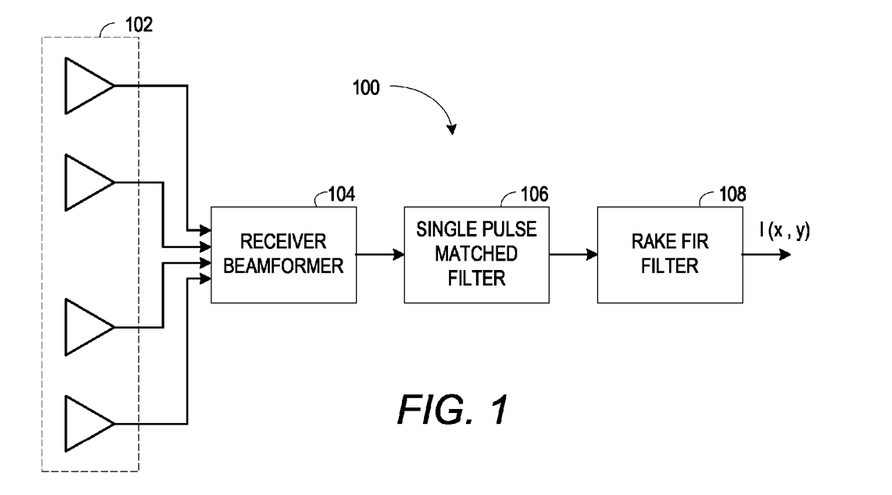
FIG. 1 is a block diagram of an example signal processing approach for ultrasound imaging, according to one embodiment.

FIG. 1 is a simplified block diagram of an example ultrasound system 100, according to one embodiment. The ultrasound signal processing arrangement 100 includes an ultrasound transducer array 102, and receive beamformer 104. The receive beamformer 104 receives the ultrasound signals from the ultrasound transducer array 102, and generates a beam sum for further processing. The ultrasound signal processing arrangement 100 in this example includes the RAKE receiver implemented as a cascade of single pulse matched filter 106, and RAKE FIR filter 108. For the ultrasound imaging application, the RAKE FIR filter 108 may be derived by decomposition of the matched filter for the predefined response function associated with a particular beam and spatial location into the convolution of a single-pulse waveform and a sequence of mathematical impulses representing the relative delays in the various paths of the channel. For the ultrasound imaging application, these delays correspond to the delays from the individual array elements to the point in space at which the reflectivity is to be reconstructed. The RAKE filter is applied to the received data at the time corresponding to the echo arrival time of the wavelet transmitted by the transducer array element nearest to the point in space to be reconstructed. Such a time will naturally include any transmit beamforming delays applied to the transducer array elements.

One implementation of the RAKE receiver sums interpolated values of the single-pulse-matched-filtered beam sum signal at the time instants indicated by the sequence of impulses. This results in N interpolations, where N is the number of elements in the ultrasound transducer array 102. The RAKE receiver may implement nearest-neighbor interpolation, for example, when the receive beamformer 102 is configured for RF beamforming. Alternatively, the RAKE receiver may implement linear interpolation, for example, when the receive beamformer 102 is configured for I/Q beamforming. In some implementations, higher order interpolations may also be used.

Another implementation of the RAKE receiver includes the RAKE FIR filter 108 having a plurality of taps. The N delays representing the propagation time from each of the N transducer array elements to the point to be imaged are converted to the coefficients of the RAKE FIR filter 108. The RAKE FIR filter 108 may be formed by accumulating the coefficients of each of the N interpolations required to interpolate the sampled beamformed data to instants between the sampling times corresponding to the propagation times from the transducer array elements to the point to be imaged. The number of taps of the RAKE FIR filter 108 varies with the spatial location of the point to be imaged, and is determined, in general, by the degree of time dispersion of the incident waveform at the image point. If spatial locations near the beam direction vector are chosen for reconstruction of the point to be imaged, the RAKE FIR filters 108 can have a number of taps less than the number of ultrasound transducer array elements N. In some implementations, where the time-dispersed incident waveform has a shorter-duration high-amplitude feature, the RAKE FIR filter can be approximated, for example, by truncating the full filter to include only those filter coefficients corresponding to high amplitude portions of the expected waveform. In such an implementation, the single-pulse matched filter may be applied as a convolution with the output data from the receive beamformer.

Figure 2:
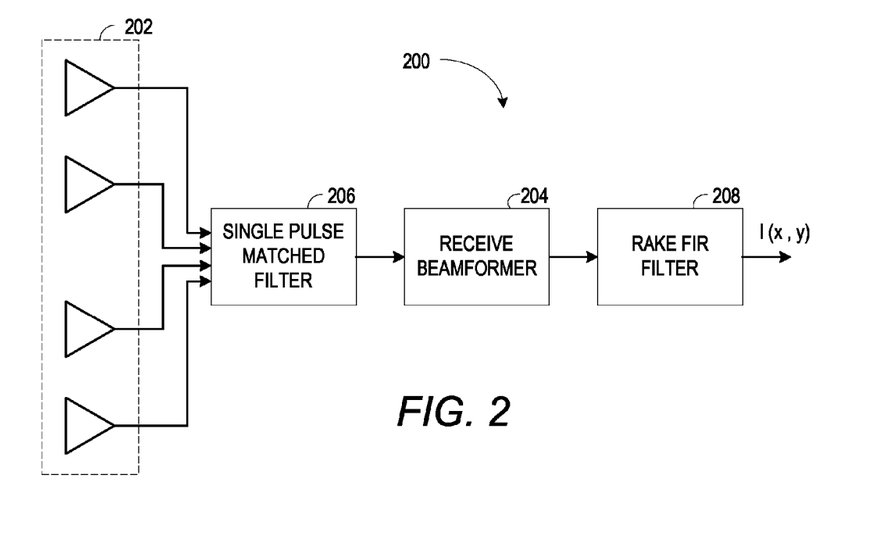
FIG. 2 is a block diagram of an example signal processing approach for ultrasound imaging, according to one embodiment.

FIG. 2 is a simplified block diagram of an example ultrasound system 200, according to another embodiment. The ultrasound signal processing arrangement 200 includes single pulse matched filter 206, RAKE FIR filter 208, and receive beamformer 204. As described above, the matched filter can be implemented as a cascade of the single-pulse matched filter 206 and the RAKE FIR filter 208. The ultrasound signal processing arrangement 200 includes the single-pulse matched filter 206 coupled to the ultrasound transducer array 202, to filter the receive element data prior to computation of the beam sum. The output of the single-pulse matched filter 206 is then applied to the receive beamformer 204. Finally, the single-pulse-matched-beam sum is applied to the RAKE FIR filter 208.

In general, the single-pulse matched filter has the shape of a waveform transmitted by a single array element, reflected by a non-distorting reflector and received by an array element. In an actual system, the shape of this waveform may not be known exactly for all probes. In both FIGS. 1 and 2, the single-pulse matched filter can be approximated by a bandpass filter for RF data or a lowpass filter for I/Q data. Such approximation of matched filters is well-known in the fields of radio and radar. Because the frequency response on both transmit and receive of the individual array element has a bandpass characteristic, it is also possible to omit the single-pulse matched filter altogether. In such an implementation, the RAKE FIR filter is still constructed as described herein.

The single-pulse matched filter may also have the shape of a waveform transmitted by a single array element, as distorted by nonlinear propagation. Such a transmitted waveform is usually considered to be linearly reflected by a non-distorting reflector and received by an array element. Alternatively, the single-pulse matched filter may have the shape of the second or higher harmonic component of such a distorted waveform. Although the shape of the distorted waveform varies with depth, the shape of the second or higher harmonic component does not. In such an implementation, the RAKE FIR filter is still constructed as described herein.

The arrangements for image reconstruction illustrated in FIG. 1 and FIG. 2 may be implemented in an image reconstruction processor. Alternatively, the implementation of the single-pulse matched filter may reside in the front end of the ultrasound system, where the analog element data is digitized. Such an implementation is illustrated in FIG. 3.

Figure 3:
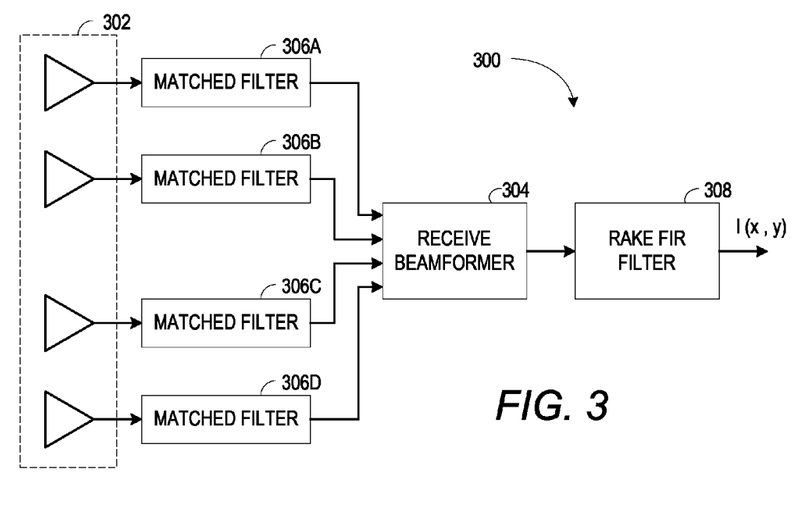
FIG. 3 is a block diagram of an example signal processing approach for ultrasound imaging, according to one embodiment.

FIG. 3 is a simplified block diagram of an example ultrasound system 300, according to one embodiment. The ultrasound processing arrangement 300 may typically be implemented where the receive beamformer 304 is implemented as an I/Q beamformer. Such an implementation is especially advantageous since a baseband-shifted version of the single-pulse matched filter can be incorporated into the I/Q converter, either in place of the lowpass filter or in cascade with a zonal lowpass filter whose pass band is wider than the bandwidth of the pulse. This reduces the computational load on the image reconstruction processor as compared with the implementations depicted in FIGS. 1 and 2. The array of ultrasound transducer elements 302 are coupled to matched filters 306, where the matched filters 306 may be a bandpass filter having a frequency response identical to the transmit/receive pulse spectrum. Any bandpass filter with approximately the same center frequency as the transmit/receive pulse spectrum, may serve as an approximate matched filters 306 for this implementation. Since the lowpass filter of the I/Q converter is equivalent to such a bandpass filter, any I/Q frontend will impose an approximate matched filter of some quality. Thus, the overall system depicted in FIG. 3 can be approximated by a system with no single-pulse matched filter, using only the RAKE FIR filter 308 in the image reconstruction.

The overall matched filter is the convolution of the transmit and receive impulse response and the transmit excitation function. The insonifying waveform is the superposition of a number of wavelets, each wavelet transmitted by a distinct element of the ultrasound transducer array 302. Each wavelet is the convolution of the excitation and the transmit impulse response. When the reflection of this waveform is measured at a single array element, another convolution with the single element receive impulse response takes place. Thus, the measured waveform is the superposition of wavelets which are the convolution of the excitation function with the convolution of the transmit and receive impulse responses. In case of a single ultrasound transducer array 302 being used as the transmit array as well as the reception array, the transmit impulse response and the receive impulse response may be the similar. In such an embodiment, the excitation function may be used as a single-pulse matched filter impulse response.

The arrangements 100, and 200, and 300 described herein, that use single-pulse matched filter 106, 206, and 306 respectively, produce an output that is equivalent to the output produced by filtering the received echo of the incident waveform using a filter whose impulse response is matched to the incident waveform as received at any transducer array element, when such a filter is applied at the output of the receive beamformer 104, 204, or 304.

Applying a temporal matched filter at the output of a receive beamformer, that is matched to a predefined response function representing the waveform echoed from the focus of the receive beamformer (in general, this is not the transmit focus), reduces the sidelobe response of the receive beamformer 104, 204, and 304. The echoes from the receive focus region are compressed such that a large portion of the energy is recovered. Whereas the echoes from the sidelobe region are spread out in time and distorted by the receive beamformer 104, 204, and 304, and so contribute a smaller amount of energy since they do not match the expected waveform of the matched filter in either shape or duration. This is true even though the incident waveform in the sidelobe region may closely resemble that in the receive focus region.

Beamforming based on RAKE receiver processing typically reduces imaging sidelobes when applied to single transmits. RAKE beamforming also enables a convenient form of retrospective transmit focusing. Rather than adding the reflections from the coherent wavefronts of several adjacent beams, the RAKE filter outputs computed for the same receive focus from multiple transmit beams are coherently summed to synthesize the effect of a focused transmit beam. The focus of the receive beamformer 102, 202, and 302 for all transmits to be combined must be the same. The predefined response functions used for the different transmits may differ. The time alignment for the individual transmissions may also differ, each RAKE filter being applied to the measured beamformed data at a time corresponding to the round-trip echo time of the transmission from the transducer array element closest to the point to be imaged, including transmit beamforming delays. Such RAKE retrospective transmit focusing eliminates the geometric modeling of the propagating wavefront that would ordinarily be needed to pre-compute the required delays for correct superposition. It also tends to produce lower imaging sidelobes relative to simple coherent superposition based on geometrical concepts.

In the RAKE beamformer, RTF synthesis is implemented by summation of short records of filtered RF data in the RF beamforming case and the summation of single samples of filtered analytic signal data in the I/Q beamforming case. In the latter case, a common phase reference for addition of reconstructed analytic signals must be defined, even though the sample window for the RAKE FIR filter may not be applied at the same delay for all transmits. In the case of RF data, demodulation of final result can be done by any form of envelope demodulation, for example lowpass filtering the square of the data in the short record obtained as an output from the matched filter. Since only a single output sample is desired, this operation is naturally structured as an inner product between a vector whose components are the squared data and a finite duration lowpass impulse response. In the case of I/Q input data, the output of the RAKE beamformer is a sample of an analytic signal, and so its modulus represents the signal envelope.

Temporal matched filtering on the insonifying pulse elongates the pulse in time and reduces the effective bandwidth of the ultrasound system. This is because the output of the single-pulse matched filter is the autocovariance of the wavelet transmitted and received from an array element. In one example, the effective length of the autocovariance function is roughly 1.4 times that of the transmitted and received pulse. Such pulse elongation produces a characteristic loss of axial resolution when the present technique is used for image formation. Thus, in some implementations an approximate matched filter may be implemented in the front end to reduce such a loss in axial resolution. Alternatively, the receive impulse response of the elements of the ultrasound transducer array 102, 202, 302 may be treated as an approximate matched filter for the transmit impulse response. Typically, the frequency spectrum of the pulse is approximately symmetric in amplitude. The only part of the overall matched filter not accounted for in this scheme is the excitation, which can be used as the single-pulse matched filter.

Figure 4:
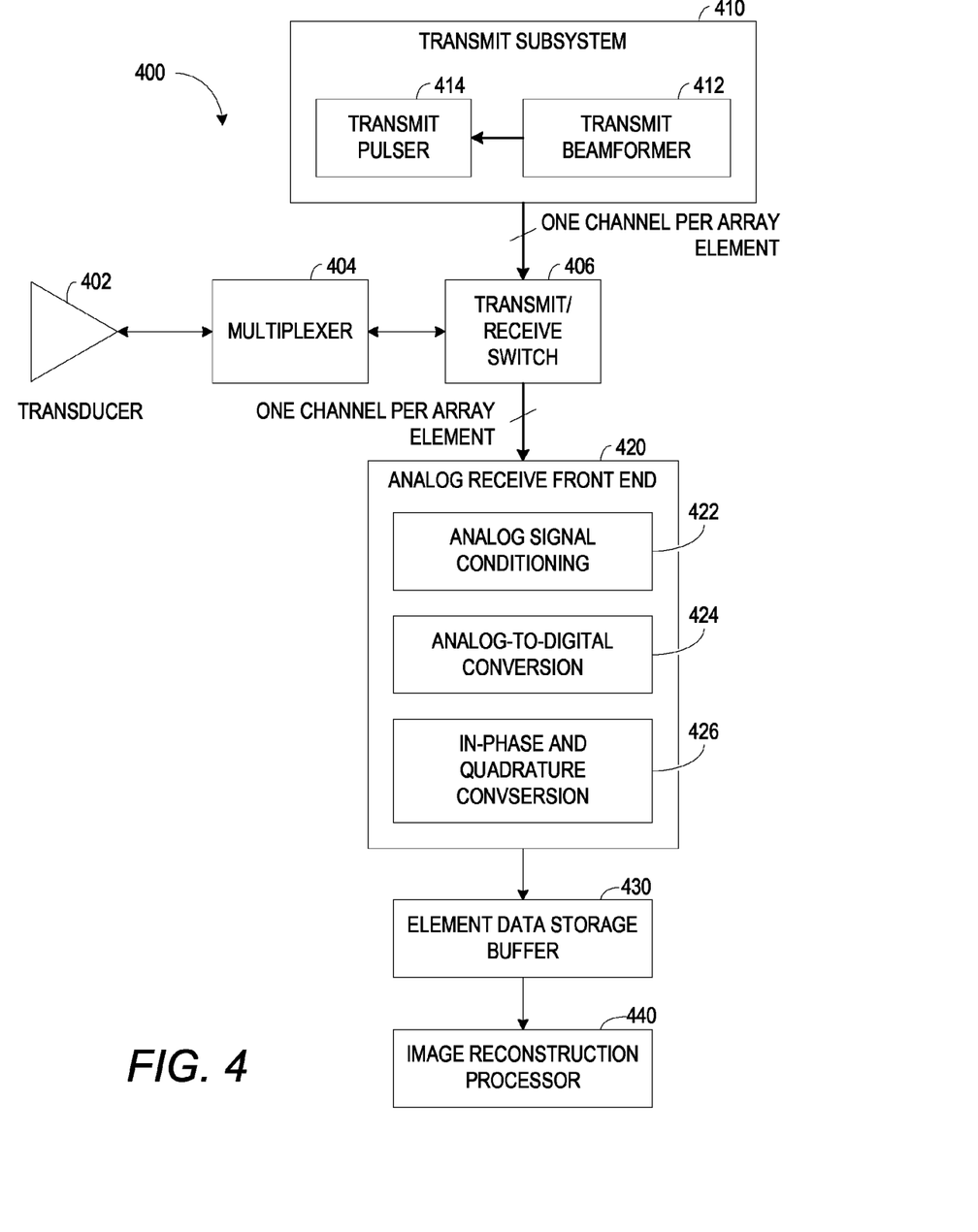
FIG. 4 is a simplified block diagram of an example ultrasound imaging system, according to one embodiment.

FIG. 4 illustrates a block diagram of an example ultrasound imaging system 400, according to one embodiment. The ultrasound imaging system 400 includes a transducer array 402, a multiplexer 404, a transmit/receive switch 406, a transmit subsystem 410 consisting of a transmit beamformer 412 and transmit pulser 414, an analog receive front end 420, an element data storage buffer 430, and an image reconstruction processor 440. The transducer array 402 may include, for example, between 8 and 512 transducer elements. The transducer elements of the transducer array 402 typically serve as transmit elements as well as receive elements. The transmit/receive switch 406 switches the transducer array 402 between a transmit mode and a receive mode. The transmit/receive switch 406 may include circuitry to protect components in the receiver section from high voltage pulses transmitted by the transmit pulsers 414. In the case of a translated-aperture system, a multiplexor 404 selects an active aperture subset of the array elements for transmission and reception. In some known systems, there are as many transmit pulsers 414 as there are elements in the active aperture. In some known systems, the receive aperture has a different size from the transmit aperture.

In the transmit mode, the transmit/receive switch 406 couples the transducer array 402 to a transmit subsystem including the transmit beamformer 412 and the transmit pulsers 414. The transmit beamformer 412 enables directional transmission of a beam of ultrasound pulses from the transducer array 402 to an object. The transmit beamformer 412 generates a control sequence for emitting ultrasound pulses from each of the transducer elements of the transducer array 402 to an object. The timing sequence triggers the transmit pulser 414 to generate high voltage pulses according to the control sequence of the transmit beamformer 412. The transmit pulser 414 then applies the high voltage pulses to the appropriate transducer element through the transmit/receive switch 406, based on the control sequence generated by the transmit beamformer 412. Thus, a spatially directional beam of ultrasound pulses is transmitted from the transducer array 402 to an object. The spatially directional beam insonifies a particular set of points within the area to be imaged, near to a line extending away from the face of the probe in the beamsteering direction. The transmit beamformer 412 insonifies the complete area to be imaged by generating different control sequences for transmitting multiple separate beams of ultrasound pulses, each beam directed in a different direction.

Upon completing transmission of one beam of ultrasound pulses, the transmit/receive switch 406 switches from the transmit mode to the receive mode. In the receive mode, the transmit/receive switch 406 couples the transducer array 402 to the analog receive front end 420. The analog receive front end 420 may include analog signal conditioning circuits 422 such as low noise amplifiers, voltage controlled amplifiers, and programmable gain amplifiers to condition the received ultrasound signals for processing. Such an analog signal conditioning circuit 422 conditions the measured ultrasound signal from every array element. After signal conditioning, the ultrasound signals are converted to digital form by analog-to-digital converters 424. The rate at which such a conversion occurs may be, for example, 50 Megasamples/sec, and the amplitude resolution may be, for example, 14 bits. The sampled ultrasound element data may then be processed by a digital in-phase and quadrature (I/Q) converter 426 into a complex-valued, low-pass representation. It is also possible for an analog I/Q converter to be applied prior to digitization. The sample rate of ultrasound data represented in such an I/Q format may be, for example, 10 Megasamples/sec, and the amplitude resolution of each component may be, for example, 16 bits.

The analog receive front end 420 may then transfer the conditioned and sampled ultrasound signals to the image reconstruction processor 440. This data transfer may take place over a data pathway such as a system bus. The output of the image reconstruction processor 440 may include envelope-demodulated image samples, and they may be transferred to further downstream components for image processing, interpolation to a required spatial sampling format or storage. The sampled ultrasound signal data may be written into a memory buffer 430 which can be accessed by the image reconstruction processor 440.

The image reconstruction processor 440 reconstructs a set of samples of an ultrasound image based on the received ultrasound element echo data. In one embodiment, the image reconstruction processor 440 may be implemented as a Graphics Processing Unit (GPU) or other high-powered, general-purpose computing device. In such an embodiment, the operations of the receive signal processor may be implemented as computer executable instructions. In another embodiment, the image reconstruction processor 440 may be implemented as hardware electronic circuits or programmable logic devices.

Figure 5:
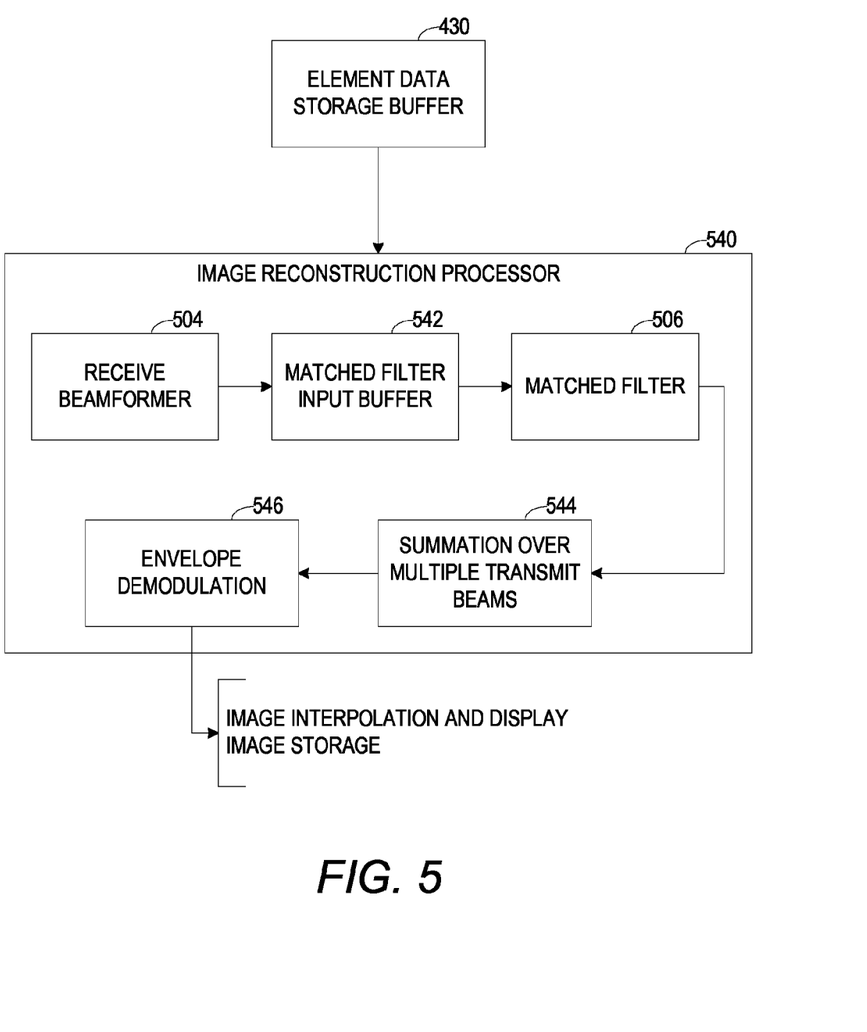
FIG. 5 is a simplified block diagram of the image reconstruction processing performed by an example ultrasound imaging system, according to one embodiment.

FIG. 5 is a simplified block diagram of an example image reconstruction processor 540, according to one embodiment. The image reconstruction processor 540 includes an implementation similar to arrangement 100 described in conjunction with FIG. 1. The input to the image reconstruction processor 540 is stored in the element data storage buffer 430. The image reconstruction processor 540 includes a receive beamformer 504, a matched filter input buffer 542 that temporarily stores the output of the receive beamformer 504 and a matched filter 506. The receive beamformer 504 produces a signal that represents echo characteristics of a point to be imaged, at a given depth and angle with respect to the transducer array 102, 202, 302, or 402.

In one embodiment, the receive beamformer 504 may be an interpolate-and-sum type digital beamformer. The receive beamformer 504 accepts a plurality of sampled input signals, each corresponding to an ultrasound transducer element. The receive beamformer 504 selects samples from each of the input signals and interpolates a sample corresponding to the delay that would be required by an analog delay-and-sum beamformer and computes a digital sum of the interpolated, delayed input signals, to obtain a beam sum of the input signals. This process is repeated, using the same receive delays, until the matched filter input buffer 542 is full.

Equation 1 shows the computations required for one possible embodiment of the receive beamformer 504 for a phased array applied to RF data. Different computations may be required for a translated aperture array, or the given computation may be used and the reconstructed points limited to the broadside look direction. Those skilled in the art will appreciate that, for beamforming of I/Q data, the analytic signal must first be reconstructed prior to the beamsum operation, requiring multiplication by complex quantities representing the carrier phase. In Equation 1, the signal $RBF_{x,y}(t,q)$ is the output of the receive beamformer focused on the point (x,y). The arguments "t" and "q" represent time from the transmit event and the transmit number, respectively. The signal denoted by $DATA_{n,q}(t)$ is the continuous time version of the received echo data from element n, received in response to transmit "q". The quantity $\tau_n(x, y)$ is the delay required to focus on the point (x, y) that is applied on array element "n". "N" is the number of array elements. The second line of the equation shows the approximation to the continuous-time beamsum implemented by linear interpolation between samples of the element echo signal, sampled at a period of $T_s$. The quantity $\alpha_n(t)$ is an interpolation coefficient determined by the time and the required delay for element "n".

$$RBF_{x,y}(t, q) = \sum_{n=1}^{N} DATA_{n,q}(t - \tau_n(x, y)) \quad \text{(Equation 1)}$$

$$\cong \sum_{n=1}^{N} \alpha_n(t) DATA_{n,q}\left(\left\lfloor \frac{t - \tau_n(x, y)}{T_s} \right\rfloor T_s\right) +$$

$$(1 - \alpha_n(t)) DATA_{n,q}\left(\left\lceil \frac{t - \tau_n(x, y)}{T_s} \right\rceil T_s\right)$$

The length of the matched filter input buffer 542 is selected based on the duration of the insonification that is incident on the point in space at which the receive beamformer 504 is focused or the length of an alternative, predefined response function. The pulse matched filter 506 is a filter whose impulse response is matched to the expected incident ultrasound waveform that would be echoed from a point to be imaged if an ideal point reflector were present at that point and received at an array element or another predefined response function. The pulse matched filter 504 may be approximated in various other ways in alternate embodiments, as noted above. The length of the matched filter input buffer 542 is selected to store such a waveform.

Next, the matched filter 506 computes an inner product, or performs a multiply/accumulate operation on the contents of the matched filter input buffer 542. Those skilled in the art will readily appreciate that this operation can be performed in a pipelined fashion with the receive beamformer 504, and that there is no need to wait until the matched filter input buffer 542 is full to begin computing the matched filter output. The summed output of the inner product operation is a complex scalar in the case of I/Q input, and it is a short record of RF data in the case of RF input data. The output of the matched filter inner product is generated using the data from a single transmit. Data from multiple transmits are coherently added together in a summation accumulator over multiple transmit beams 544.

Equation 2 describes the output of the summation accumulator 544 for reconstruction of the reflectivity at spatial location (x, y) according to one example. The signal $RBF_{x,y}(t, q)$ is the output of the receive beamformer focused on the point (x, y), defined by Equation 1, K samples of which have been computed and stored in the matched filter input buffer 542. The arguments of $RBF_{x,y}(t, q)$ represent time from transmit and the transmit number. The signal is sampled, and the time argument is quantized with period $T_s$. The precomputed K-component vector $MF_{x,y,q}$ is the discrete-time matched filter impulse response used to reconstruct the reflectivity at (x, y) for transmit number q. Note that this matched filter impulse response varies from point to point in space and from transmit to transmit; this is because each such combination of conditions can cause a different expected reflection.

$$SA_{x,y}(t) = \sum_{q=1}^{Q} \sum_{k=1}^{K} MF_{x,y,q}(k) RBF_{x,y}(k+t, q) \qquad \text{(Equation 2)}$$

It is important to note that, in order for the coherent sum given by Equation 2 to be meaningful in the case of I/Q in put signals, the receive beamformer 504 should use the same timebase for analytic signal reconstruction for all transmits. This is equivalent to using a consistent carrier phase for all transmits.

The output of the image reconstruction processor 540 is a single sample of an envelope-demodulated ultrasound image. The quantity in Equation 2 is converted into an envelope demodulated image by one of two procedures. Envelope demodulation 546 is performed in the case of I/Q input data by taking the modulus of the scalar output of the multiple transmit accumulation buffer. Envelope demodulation 546 is performed in the case of RF input data by taking the short time record accumulated in the summation accumulator 544, squaring it and forming its inner product with a lowpass finite impulse response. An image is formed by repeating the processing steps leading to a single sample output for a number of locations on an image plane or sample volume.

In the case of envelope demodulation 546 applied to the output of an analytic signal interpolation beamformer applied to I/Q input data, the output image sample can be expressed as $I(x, y) = |SA_{x,y}(T_0)|^2$. The quantity $T_0$ is a time offset that is related to the depth of the location (x, y).

In the case of envelope demodulation 546 applied to the output of an interpolation beamformer applied to RF data, the output image sample can be expressed by Equation 3. The quantity $SA_{x,y}(t)$ is defined by Equation 2. Samples of this signal are produced at the RF sample rate. The precomputed vector LPF(t) represents a convenient lowpass filter impulse response of length T samples.

$$I(x, y) = \sum_{t=1}^{T} SA_{x,y}^2(t) LPF(t) \qquad \text{(Equation 3)}$$

Figure 6:
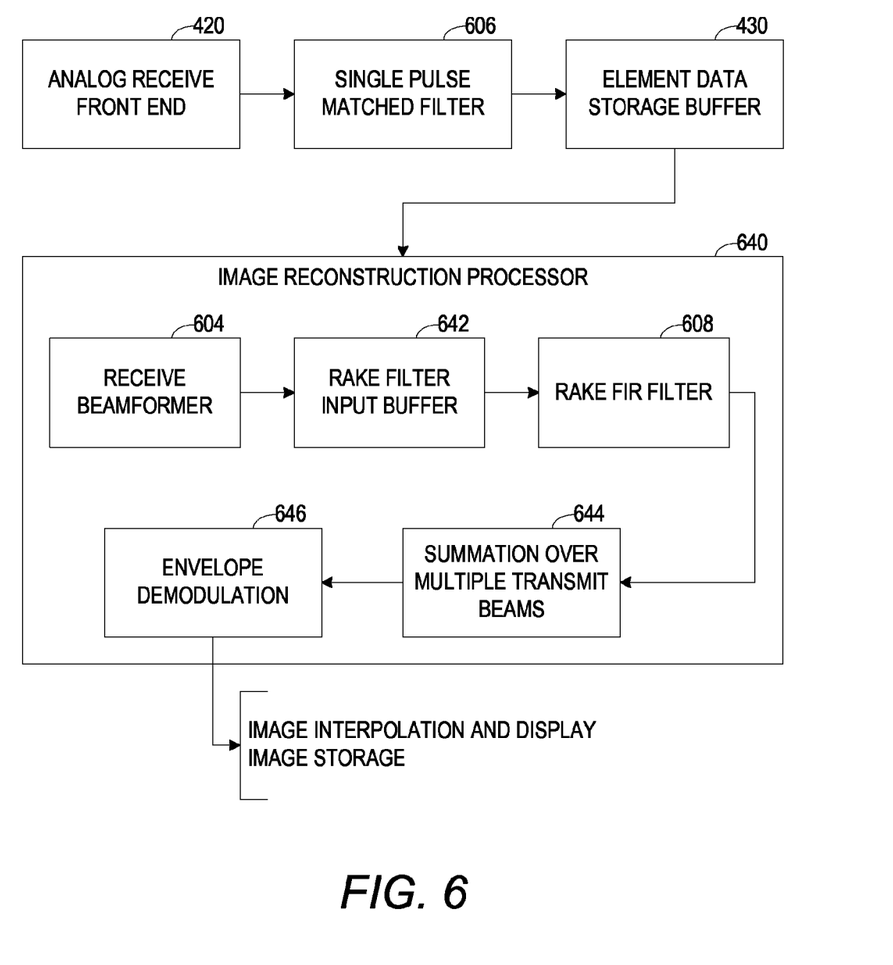
FIG. 6 is a simplified block diagram of the image reconstruction processing performed by an example ultrasound imaging system, according to one embodiment.

FIG. 6 is a simplified block diagram of an example image reconstruction processor 640, according to one embodiment. The image reconstruction processor 640 includes an implementation similar to arrangements 200 or 300 described in conjunction with FIG. 2 and FIG. 3, respectively. The conditioned and sampled output of the analog receive frontend 420 is matched filtered by a single-pulse matched filter 606. In some implementations, the matched filter 606 may be an approximate matched filter. Alternatively, the matched filter 606 may be combined with an I/Q converter as part of the analog receive frontend 420. The output of the single-pulse matched filter 606 is stored in the element data storage buffer 430. The data in the element data storage buffer 430 is available to the receive signal processor 640, for example by way of a memory read. The image reconstruction processor 640 includes a receive beamformer 604, a RAKE filter input buffer 642 that temporarily stores the output of the receive beamformer 604, and a RAKE FIR filter 608. The receive beamformer 604 produces a signal that represents echo characteristics of a point to be imaged, at a given depth. In one embodiment, the receive beamformer 604 may be an interpolate-and-sum type beamformer. The receive beamformer 604 accepts a plurality of sampled input signals, each corresponding to an ultrasound transducer element. The receive beamformer 604 selects samples from each of the single-pulse matched filtered input signals and interpolates a sample corresponding to the delay that would be required by an analog delay-sand-sum beamformer and computes a sum of the interpolated, delayed input signals, to obtain a beam sum of the matched filtered input signals. This process is repeated, using the same receive delays, until the RAKE FIR filter input buffer 642 is full.

In some embodiments, the length of the RAKE FIR filter input buffer 642 is determined by the duration of the insonification that is incident on the point in space at which the receive beamformer is focused. In some other embodiments, the length of the RAKE FIR filter input buffer is determined by a filter that approximates the insonification waveform in some way, for example by selecting only the high-amplitude part. The pulse matched filter 606 is a filter whose impulse response is matched to the expected incident ultrasound waveform that would be echoed from a point to be imaged is an ideal point reflector were present at that point, and received at a single array element. The length of the RAKE filter input buffer 642 is great enough to store such a waveform.

The RAKE FIR filter 608 computes an inner product, or performs a multiply/accumulate operation on the contents of the RAKE filter input buffer 642. Those skilled in the art will readily appreciate that this operation can be performed in a pipelined fashion with the receive beamformer 604, and that there is no need to wait until the buffer 642 is full to begin computing the RAKE FIR filter 608 output. The summed output of the inner product operation is a complex scalar in the case of I/Q input, and it is a short record of RF data in the case of RF input data. The output of the RAKE FIR filter 608 inner product is generated using the data from a single transmit. Data from multiple transmits is coherently added together in a summation accumulator 644. The output of the summation accumulator 644 is envelope demodulated 646, as described herein, to form an output sample.

The difference between the two embodiments depicted in FIG. 5 and FIG. 6 is the decomposition of the overall matched filter of FIG. 5 into a single-pulse filter 506 and a RAKE FIR filter 608 in FIG. 6, and the relocation of the single-pulse matched filter 606 to the output of the receive frontend 420. The two configurations produce the same outputs. To demonstrate this equivalence, Equation 4 shows the continuous-time version of the matched filter of Equation 2 decomposed into the convolution of a single transmit/receive pulse and a sum of impulse functions representing the arrival time offsets of the N wavelets from the N transmit array elements. The arrival time offsets are determined by the sum of the single-element propagation times to the point at which the receive beamformer is focused and the transmit beamforming delays. This is the form of the insonifying waveform at the point (x, y) as received by a single array element. D is the duration of the pulse, P(t).

$$MF_{x,y,q}(t) = \sum_{m=1}^{N} P(t - \Delta_m) \qquad \text{(Equation 4)}$$

-continued $$= \sum_{m=1}^{N} \int_D P(\tau)\delta(\tau - \Delta_m)d\tau$$

$$= \int_D P(\tau)\left[\sum_{m=1}^{N} \delta(\tau - \Delta_m)\right]d\tau$$

Now the sum of impulses in brackets in Equation 4 can be interpolated to a regularly spaced set of sample times, producing an FIR filter. This corresponds to interpolating the value of $P(t-\Delta_m)$ from the sample values preceding and following it. Note that the RAKE FIR filter contains all of the information that is unique to the location to the imaged and the focal characteristics of the transmit beam at that point. Substituting the RAKE FIR filter of length D for the sum of impulses above and writing the resulting discrete time with the pulse represented by P samples, produces $$MF_{x,y,q}(k) = \sum_{d=1}^{D} P(k-d)RAKE_{x,y,q}(d) \quad \text{(Equation 5)}$$

Equation 6 starts with Equation 2, representing the approach of FIG. 5, and substitutes Equation 5 and Equation 1. The final line of Equation 6 has the same form as does Equation 2, except that the measured element data is replaced by single-pulse filtered element data, denoted by $MFD_{n,q}$, and the overall matched filter is replaced by the RAKE FIR filter of Equation 5.

$$SA_{x,y}(t) = \sum_{q=1}^{Q} \sum_{k=1}^{K} MF_{x,y,q}(k)RBF_{x,y}(k+t,q) \quad \text{(Equation 6)}$$

$$= \sum_{q=1}^{Q} \sum_{d=1}^{D} RAKE_{x,y,q}(d) \sum_{n=1}^{N}$$

$$\left[\sum_{k=1}^{K-D+1} DATA_{n,q}(t+k+d - \tau_n(x, y))P(k)\right]$$

$$= \sum_{q=1}^{Q} \sum_{d=1}^{D} RAKE_{x,y,q}(d)$$

$$\sum_{n=1}^{N} MFD_{n,q}(t+d - \tau_n(x, y))$$

The sample rate at the output of the receive beamformer may be chosen according to the requirements of the image reconstruction processor 440. In one embodiment, the sample rate may be chosen to minimize the length of the RAKE FIR filter or the overall matched filter while still maintaining acceptable interpolation error.

The disclosed methods can be embodied in the form of computer or controller implemented processes and apparatuses for practicing these processes. These methods can also be embodied in the form of computer program code containing instructions embodied in tangible media, such as floppy diskettes, CD-ROMs, hard drives, and the like, wherein, when the computer program code is loaded into and executed by a computer or controller, the computer becomes an apparatus for practicing the method. The methods may also be embodied in the form of computer program code or signal, for example, whether stored in a storage medium, loaded into and/or executed by a computer or controller, or transmitted over some transmission medium, such as over electrical wiring or cabling, through fiber optics, or via electromagnetic radiation, wherein, when the computer program code is loaded into and executed by a computer, the computer becomes an apparatus for practicing the method. When implemented on a general-purpose microprocessor, the computer program code segments configure the microprocessor to create specific logic circuits.

While the invention has been described in considerable detail with reference to a few exemplary embodiments only, it will be appreciated that it is not intended to limit the invention to these embodiments only, since various modifications, omissions, additions and substitutions may be made to the disclosed embodiments without materially departing from the scope of the invention. In addition, many modifications may be made to adapt to a particular situation or an installation, without departing from the essential scope of the invention. Thus, it must be understood that the above invention has been described by way of illustration and not limitation. Accordingly, it is intended to cover all modifications, omissions, additions, substitutions or the like, which may be included within the scope and the spirit of the invention as defined by the claims.

The invention claimed is:

1. A system for ultrasound imaging, comprising:
   an analog to digital converter for digitizing ultrasound echo signals from a plurality of transducer elements in response to ultrasound transmit beams;
   a matched filter for filtering the digitized ultrasound echo signals;
   a first buffer for storing the ultrasound echo signals;
   a beamformer for computing beam sums of the ultrasound echo signals, wherein the beamformer is focused at a point to be imaged,
   a second buffer for storing into a time record a plurality of said beam sums corresponding to multiple instants of time in a time window;
   a second filter for filtering the time record based, at least in part, on a predetermined response function; and
   a processor to reconstruct a set of image samples, the processor performing the following for at least a portion of the set of image samples:
       computing a coherent sum of at least one of the beam sums in the filtered time record; and
       demodulating the coherent sum to form an output image sample corresponding to the point to be imaged.

2. The system of claim 1, wherein the matched filter utilizes a transmit impulse response, receive impulse response, transmit excitation applied to transducer elements or serial combinations thereof.

3. The system of claim 1, wherein the matched filter is a bandpass filter centered around second or higher harmonic frequency of the ultrasound transmit beams.

4. The system of claim 1, wherein the matched filter is a bandpass filter centered around a center frequency of the ultrasound transmit beams.

5. The system of claim 1, wherein the predetermined response function comprises an expected ultrasound echo signal.

6. The system of claim 1, wherein the matched filter comprises a single pulse matched filter for single pulse match filtering the time record based on the predetermined response function; and the second filter comprises a RAKE Finite Impulse Response (FIR) filter for filtering the single pulse match filtered time record.

7. The system of claim 1, wherein the predetermined response function comprises a RAKE Finite Impulse Response (FIR) or an approximated RAKE Finite Impulse Response (FIR).

* * * * *